(12) United States Patent
Van Beek et al.

(10) Patent No.: US 7,663,748 B2
(45) Date of Patent: Feb. 16, 2010

(54) AUTOFOCUS MECHANISM FOR SPECTROSCOPIC SYSTEM

(75) Inventors: Michael Cornelis Van Beek, Eindhoven (NL); Gerald Lucassen, Eindhoven (NL); Marjolein Van Der Voort, Valkenswaard (NL); Wouter Harry Jacinth Rensen, Eindhoven (NL); Durk Jolmer De Vries, Nijega (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 376 days.

(21) Appl. No.: 11/570,132

(22) PCT Filed: Jun. 7, 2005

(86) PCT No.: PCT/IB2005/051848

§ 371 (c)(1),
(2), (4) Date: Dec. 7, 2006

(87) PCT Pub. No.: WO2005/124423

PCT Pub. Date: Dec. 29, 2005

(65) Prior Publication Data

US 2007/0252984 A1  Nov. 1, 2007

(30) Foreign Application Priority Data

Jun. 17, 2004  (EP)  ................................. 04102769

(51) Int. Cl.
*G01J 3/30* (2006.01)
(52) U.S. Cl. ..................................... 356/317
(58) Field of Classification Search ................ 356/317; 250/201.4
See application file for complete search history.

(56) References Cited

U.S. PATENT DOCUMENTS

| | | | |
|---|---|---|---|
| 4,625,103 A | 11/1986 | Kitamura et al. | |
| 5,270,527 A | 12/1993 | Salzmann | |
| 5,932,872 A * | 8/1999 | Price | 250/201.3 |
| 5,962,238 A * | 10/1999 | Sizto et al. | 436/172 |
| 6,069,690 A | 5/2000 | Xu et al. | |
| 6,609,015 B2 | 8/2003 | Lucassen et al. | |
| 7,202,953 B1 * | 4/2007 | Mueller et al. | 356/301 |
| 2002/0044346 A1 | 4/2002 | Nguyen et al. | |
| 2003/0109774 A1 * | 6/2003 | Lucassen et al. | 356/301 |
| 2004/0129858 A1 | 7/2004 | Czarnetzki et al. | |

FOREIGN PATENT DOCUMENTS

| | | |
|---|---|---|
| WO | 9009756 A1 | 9/1990 |
| WO | 9840723 A1 | 9/1998 |

(Continued)

*Primary Examiner*—Kara E Geisel

(57) ABSTRACT

An autofocus mechanism for a spectroscopic system determines a time varying optical property of a volume of interest. The mechanism measures the fluctuations of the optical property of the volume of interest for determining the position of the volume of interest. The spectroscopic system focuses an excitation beam into the determined volume of interest and collects return radiation emanating from the volume of interest for spectroscopic analysis. Preferably, inelastically scattered radiation of an excitation beam is separated from elastically scattered radiation for spectroscopic analysis. The elastically scattered radiation of the excitation beam is measured for fluctuations of the optical property of the volume of interest. A control loop maximizes the amplitude and/or intensity of the fluctuations and specifies the position of a volume of interest e.g. the center of a capillary vessel.

20 Claims, 5 Drawing Sheets

FOREIGN PATENT DOCUMENTS

Figure 1:
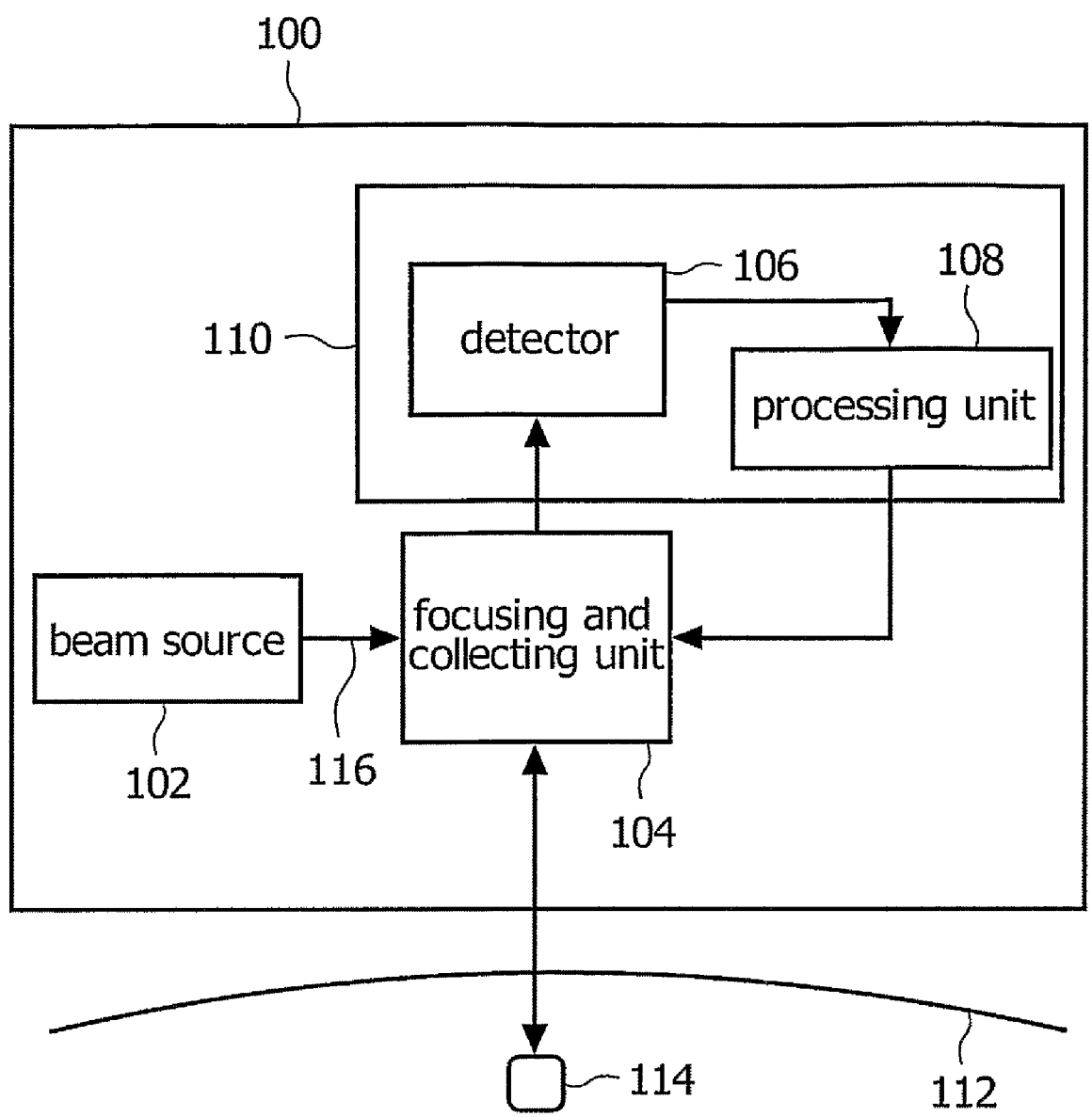

| | | | |
|---|---|---|---|
| WO | 0139665 | A2 | 6/2001 |
| WO | 02057758 | A1 | 7/2002 |
| WO | 02057759 | A1 | 7/2002 |
| WO | 2004081549 | A1 | 9/2004 |
| WO | 2004082474 | A1 | 9/2004 |
| WO | 2005015179 | A1 | 2/2005 |

* cited by examiner

AUTOFOCUS MECHANISM FOR SPECTROSCOPIC SYSTEM

The present invention relates to the field of spectroscopic analysis of a volume of interest.

Usage of optical spectroscopic techniques for analytical purposes is as such known from the prior art. WO 02/057758 A1 and WO 02/057759 A1 show spectroscopic analysis apparatuses for in vivo non-invasive spectroscopic analysis of the composition of blood flowing through a capillary vessel of a person. Preferably, spectroscopic analysis is realized by making use of confocal Raman spectroscopy to measure the concentration of analytes in blood in vivo. For acquiring a high signal to noise ratio or signal to background ratio of a detectable spectroscopic signal, it is advantageous that the confocal measurement volume is completely or at least largely located inside a blood vessel. This requires a precise determination of the location of blood capillaries underneath the surface of the skin of the person. Because a confocal detection scheme is used, not only the lateral position of the blood capillary but also the depth of the blood capillary below the skin surface has to be known.

Blood capillaries located close to the skin surface typically have a diameter of about 10 µm. The confocal measurement volume of for example Raman signals can be well confined in all three dimensions inside a volume that can be as small as 5×5×5 µm$^3$. Positioning of such a small confocal measurement volume into the center of a typical blood capillary allows for collecting of spectroscopic signals featuring negligible background signal from surrounding skin tissue. Precise positioning of the confocal measurement volume into the center of a capillary vessel requires a positioning resolution of around 1 µm in all three dimensions.

Moreover, since acquisition of spectroscopic data requires at least a couple of seconds a potential movement of the person during acquisition of the data has to be taken into account. It is therefore necessary, that the spectroscopic system keeps track of such movements in order to maintain the position of the confocal measurement volume inside a selected capillary vessel.

Spectroscopic systems for non-invasive in vivo blood analysis making use of a confocal detection scheme require a sufficient tracking of the confocal measurement volume for determining the location of a capillary vessel as well as for following any movement of the capillary vessel. Determination of the lateral position of a capillary vessel, i.e. a volume of interest, effectively makes use of imaging techniques such as confocal laser scanning microscopy (CLSM) or orthogonal polarized spectral imaging (OPS imaging).

The CLSM technique is based on scanning of a laser spot through a skin volume in all three spatial directions. Capillary vessels and in particular blood vessels can effectively be recognized because of their different reflection properties compared to the surrounding tissue. Since CLSM makes use of a confocal detection scheme, the depth of the blood vessel, i.e. the distance from the skin surface, can be accurately determined. Such a CLSM system is rather expensive and large in size and operates with a fairly low frame rate. Consequently, determination of the location of a blood vessel becomes very time intensive.

OPS imaging in turn is based on scattering of light inside the skin. Because of absorption of light in blood, a blood vessel appears dark in an OPS image. Making use of such an imaging technique featuring a low numerical aperture (NA), allows to acquire a relatively large lateral area of a volume of the skin. Such a lateral image is sufficient for determination of the lateral position of a blood vessel but due to the low numerical aperture, the depth of focus is rather large. Hence, the depth of an imaged blood vessel can only be determined insufficiently. Thus OPS imaging provides a precise lateral position determination of a blood vessel but only a rough determination of the depth of the blood vessel.

In contrast to the imaging system, acquisition of spectroscopic data from a small confocal measurement volume requires a high numerical aperture for generating a sufficiently small focus spot in all three spatial directions. Additionally, making use of a high numerical aperture allows for realization of a high depth resolution.

The document WO 01/39665 A2 discloses a method and an apparatus for maintaining depth and position of focus of a Raman excitation source, regardless of whether an imaging light collection system is used. The method and apparatus provide a way to obtain spectroscopic information from living tissue of a subject. This method comprises irradiating a tissue of interest in a subject with light having an excitation wavelength that passes from a light source through a first adjustable lens, and passing spectra that are emitted by the tissue through a second adjustable lens. The spectra that are passed through the second adjustable lens are then collected and analyzed to determine a target signal associated with an analyte of interest. The method comprises deriving a correction signal from the target signal, and adjusting the position of the first adjustable lens or the second adjustable lens on the basis of the correction signal so as to enhance the target signal.

Preferably, this method makes use of Raman spectroscopy and in particular of analyzing spectra and adjusting the position of a lens in order to enhance a target signal determined by the spectra. This method and apparatus makes use of two separate lenses for irradiating a tissue of interest by an excitation beam and for collecting spectra that are emitted by the tissue.

It is therefore obvious to make use of the Raman spectrum for depth alignment of the confocal measurement volume. Analysis of the Raman spectrum in fact indicates the amount of blood and/or surrounding tissue in the measurement volume. However, this has one major disadvantage. Since Raman scattering is an extremely inefficient process, it takes at least several seconds to collect a sufficient spectroscopic signal that allows to discriminate between blood and skin tissue. Due to such a long time interval, analysis of the spectroscopic signal for tracking of a blood vessel is almost completely insufficient. The tracking system would simply be too slow to follow a person movement. Eventually reducing the readout cycle of the detector detecting the spectroscopic signal, i.e. a charge coupled device (CCD) chip, would critically enhance the readout noise of the acquired spectroscopic data.

The invention therefore provides an improved autofocus mechanism for alignment of depth of a confocal measurement volume of a spectroscopic system for determining a property of a volume of interest.

The invention provides a spectroscopic system for determining of a property of a volume of interest. The volume of interest has an optical property varying with time and the spectroscopic system comprises a measurement unit for determining the position of the volume of interest on the basis of measuring of an optical property of at least first and second volumes during a first and second time interval. The spectroscopic system further comprises focusing means for focusing an excitation beam into the volume of interest and detection means for detecting return radiation from the volume of interest for spectroscopic analysis.

The invention makes effective use of the optical properties of the volume of interest. In particular the invention makes effective use of a temporal variation or temporal fluctuations of optical properties of biological structures of biological substances, such as e.g. blood and in particular red blood cells. In the near infrared (NIR) wavelength range, the reflectivity of red blood cells is remarkably larger than the reflectivity of blood plasma. Therefore, by directing a NIR beam inside a blood capillary, a strong fluctuation of the amount of elastically scattered light, i.e. reflected light, can be observed if red blood cells flow through the capillary. In the absence of a blood cell, the reflection is low. It increases remarkably when a red blood cell passes the capillary irradiated by NIR radiation. Since red blood cells have a doughnut shape geometry that is comparable to the size of a typical confocal measurement volume of the spectroscopic system, the amount of reflected light strongly depends on the presence or absence of red blood cells. By assuming typical parameters for the diameter of the blood capillary, the blood flow and the red blood cell concentration, the flux of red blood cells inside a blood capillary can be determined around a few hundred of cells per second.

Consequently, strong fluctuations in the intensity of reflected light may occur on a time scale of milliseconds. Preferably, the optical property of the fluid flowing through the biological tubular structure is determined by elastic scattering, i.e. reflection, of the excitation beam and not by analyzing the spectroscopic signal, i.e. the return radiation, that is frequency shifted with respect to the excitation beam due to inelastic scattering processes, such as Stokes or anti-Stokes scattering.

Preferably, the lateral position of the volume of interest is determined by a separate imaging system such as Orthogonal Polarized Spectral Imaging (OPSI), Confocal Video Microscopy (CVM), Optical Coherence Tomography (OCT), Confocal Laser Scanning Microscopy (CLSM), Doppler based imaging and ultrasound based imaging. Corresponding imaging techniques are disclosed U.S. 60/262,582, U.S. Ser. No. 09/912,127, U.S. Ser. Nos. 10/549,056 and 10/567,284, the entirety of which is herein incorporated by reference.

Measuring of the optical property of at least a first and a second volume during a time interval is preferably exploited in order to determine the depth of the volume of interest, hence to determine the position of the plane into which the excitation beam has to be focused in order to ideally match the volume of interest. Therefore, at least one of the at least first and second volumes have to at least partially overlap with the volume of interest. The determined optical properties of the at least first and second volumes are indicative of the degree of overlap between the first and second volumes and the volume of interest. Since, the position of the at least first and second volumes is known, the position of the volume of interest can be sufficiently determined. For example, even when the first volume partially overlaps with the volume of interest while the second volume does not overlap at all with the volume of interest, a sufficient determination of the position of the volume of interest is principally possible.

Once the position of the volume of interest has been determined by exploiting the optical property of e.g. a biological fluid, the focusing means of the spectroscopic system are adapted to focus the excitation beam into the volume of interest. Furthermore, the spectroscopic system makes use of its detection means for acquiring spectroscopic data from the volume of interest specifying a particular structure or a particular substance, such as e.g. a blood vessel.

According to a further preferred embodiment of the invention, the measurement unit is further adapted to detect at least a first and a second measurement return radiation from the least first and second volumes. The first and second measurement return radiation is indicative of the optical property of the first and second volumes. This first and second measurement return radiation emanates from the first and second volumes. In particular, when either one of the first or second volumes at least partially overlaps with the volume of interest the position of the volume of interest can be sufficiently determined.

The measurement radiation can be generated on the basis of a separate light source that provides a different radiation than the excitation radiation. For example, light that is generated by an imaging system can be used. Alternatively, a separate light source can be implemented that exclusively serves to provide the irradiation of the first and second volumes in order to generate sufficient measurement return radiation.

Moreover, radiation of the excitation beam that is elastically scattered at the first and second volumes can be effectively used as first and second return radiation. In this way, the existing light source for generating the excitation beam can be effectively exploited.

Preferably, the position and in particular the depth of the at least first and second volumes can be arbitrarily shifted allowing to measure the elastic scattering at different positions e.g. underneath the surface of the skin. High fluctuations in the elastic scattering signals indicate a flow of red blood cells and hence a substantial overlapping of the at least first and second volumes with a blood vessel defining a volume of interest.

In contrast, low fluctuations in the at least first and second measurement return radiation indicate that the at least first and second volumes do not overlap with a blood vessel or only slightly overlap with a blood vessel. Since the positions of the at least first and second volumes are well defined, by analyzing optical signals that are indicative of an overlap between the first and second volumes with a dedicated volume of interest, the position of the volume of interest can be precisely determined.

The position of the volume of interest can therefore precisely be determined. Preferably, the lateral position determination is governed by means of conventional imaging techniques and the inventive determination of the position of the volume of interest refers to the depth of the volume of interest, e.g. the depth underneath the surface of a skin of a person.

Further, the inventive determination of the position of the volume of interest is by no means restricted to depth determination. In principle, the measurement unit can be universally adapted to determine also any lateral position of the volume of interest on the basis of fluctuations of an optical property of a volume of interest.

According to a further preferred embodiment of the invention, the first and second time intervals either completely coincide or partially coincide or the first and second time intervals define two non-coinciding sequential time intervals.

When the first and the second time intervals coincide, the optical properties of the at least first and second volumes are determined simultaneously. Hence, a degree of overlap between the first and the second volume with the volume of interest is determined during the same time interval. Having knowledge of the approximate size of the volume of interest and having further knowledge of the mutual separation and relative position of the first and second volumes, allows to determine the position of the volume of interest on the basis of a single simultaneous measurement of the optical property of the at least first and second volumes.

The other extreme, where the first and the second time intervals do not coincide at all, hence the first and the second volumes are investigated sequentially, refers to a spatial scanning of the at least first and second volumes. Principally, the first volume is successively scanned through the volume of interest and corresponding optical signals referring to different positions of the first volume are measured. A maximum of the measured signal then indicates a maximum overlap between the first volume and the volume of interest. The corresponding position of the first volume then refers the center of the volume of interest.

For example measuring of fluctuations of elastically scattered light that is scattered at different locations that vary in depth effectively allows for retrieving and for tracking the center of a capillary vessel. Since fluctuations of e.g. a blood stream occur on a time scale of milliseconds, the frame rate for scanning is sufficiently high allowing for an effective determination and tracking of the position of the volume of interest.

According to a further preferred embodiment of the invention, the measurement unit is further adapted to determine the maximum amplitude of the temporal variations of the at least first and second measurement return radiation. Acquiring fluctuations of radiation that is elastically scattered from a plurality of different volumes allows to find a particular volume from which the largest fluctuations in elastic scattering emanate.

Assuming that the diameter of a typical blood capillary is substantially equal to the dimensions of a red blood cell, it can be concluded that a single blood cell entirely fills the diameter of a blood vessel. When the size of the confocal measurement volume of the measurement beam is in the same range as the size of a red blood cell, the maximum of intensity fluctuations of the measurement return radiation arises, when the measurement volume of the measurement beam substantially overlaps with the center of the capillary vessel. Consequently, the depth of focus needed for determination of the volume of interest of a spectroscopic system can effectively be determined by performing a depth scan with the help of a measurement radiation and subsequently determining the maximum intensity fluctuations of the elastically scattered light emanating from the various volumes being irradiated during the depth scan.

According to a further preferred embodiment of the invention, the measurement unit is further adapted to determine a difference between the amplitude of the temporal variations of the first and the second measurement return radiation. In this embodiment, only the elastically scattered light emanating from two volumes has to be analyzed. This is preferably applicable when first and second time intervals substantially coincide. The two locations have the same lateral co-ordinates but slightly differ in depth. Preferably, the distance between the first and the second volume is slightly below the typical diameter of a blood vessel. Collecting and analyzing measurement return radiation that is elastically scattered at the first and the second volumes provides two optical signals featuring temporal fluctuations. It can be assumed that the frequency of the fluctuations of the first and the second signal is substantially equal but that the magnitude of the fluctuations differ between the first and the second signal.

Especially the magnitude of the fluctuation of the first signal is an indication for the degree of overlap of the first volume and the blood vessel. For the second intensity signal a similar assumption holds. Assuming further a kind of circular shape of the blood vessel the conclusion can be drawn, that the first and the second volumes are equally spaced from the center of the blood vessel when the fluctuations of the first and the second intensity signal are equal in magnitude.

In this way measuring and comparing the magnitude of the fluctuations of the first and the second intensity signal enables the generation of a control signal being indicative of the relative position of the first and/or the second volumes with respect to the center of the blood vessel. Here, the control signal is simply the difference between the amplitude of the first intensity signal and the amplitude of the second signal. Providing the control signal to a control mechanism that is adapted to control the focusing unit, allows to establish a control loop for minimizing the control signal, hence to position the first and the second volumes centrally around the center of a blood vessel. Having knowledge of the coordinates of the first and the second volumes, it is straight forward to direct the excitation beam into the volume of interest which is then defined by the geometric center of the first and the second volumes.

According to a further preferred embodiment of the invention, the measurement beam and the excitation beam are generated by the same optical source. Furthermore, the excitation beam and the measurement beam are focused by the same focusing unit. It is even of practical use that the measurement beam is actually a part of the excitation beam. When for example a Raman spectroscopic technique is applied in the spectroscopic system, it can be assumed that the plurality of scattering processes occurring in the sample and in particular in a confocal measurement volume of the spectroscopic system are of elastic nature.

Hence a major part of the scattered radiation is elastically scattered in the confocal measurement volume and can be used for the above mentioned fluctuation measurement. A minor part of the back scattered and collected radiation is subject to frequency shifting due to inelastic scattering processes. These frequency shifted components are preferably spatially separated from the elastically scattered components for spectroscopic analysis of the sample.

According to a further preferred embodiment of the invention, the measurement unit comprises at least one detector element and at least one aperture element that forms an aperture for the at least first and second measurement return radiation. The measurement unit for detecting elastically scattered radiation emanating from the at least first volume typically makes use of an arrangement that provides an easy and effective shifting of the at least first and second volumes that are subject to elastic scattering measurement. By shifting the aperture and the detector the position of the at least first and second volumes can be shifted. The detector element can be implemented by any kind of photo detector and does not have to provide a spatial resolution. Its frame rate must be large enough in order to resolve the temporal fluctuations of the reflected light, that is typically in the range of milliseconds. Conventional commercially available photo diodes generally fulfill these requirements.

The aperture element can be any kind of aperture, such as e.g. a pinhole or the aperture of an optical fiber even allowing to transmit the optical signal to a remote location. Alternatively, the functionality of the detector element and the aperture element can be merged in a pinhole sized photo diode.

According to a further preferred embodiment of the invention, the at least one detector element and the at least one aperture element being adapted to be moveable along the optical axis of the at least first and second measurement return radiation. In this way the position of the at least first and second volumes can be arbitrarily shifted. This allows to vary the relative distance between the first and the second volumes in order to adapt the measurement unit to volumes of interest that are different in size. Also the depth position of the first and the second volumes can be modified without the necessity of moving the objective lens of the spectroscopic system.

According to a further preferred embodiment of the invention, the first and the second volumes as well as the center of a measurement volume into which the excitation beam is focused are located on the optical axis of the excitation beam. In this way, the position of the first and the second volumes can only be shifted on the optical axis of the excitation beam. This can be effectively realized by modification of the corresponding aperture along the optical axis of the radiation being reflected at the first and the second volumes Measuring of the optical properties of the fluid at the first and the second volumes is therefore of practical use to implement an autofocus mechanism for the spectroscopic system for precisely retrieving and tracking a distinct capillary vessel.

According to a further preferred embodiment of the invention, the first and the second volumes are substantially equidistantly separated from the center of the measurement volume. By precisely determining the position of the first and the second volumes that specify a certain overlap with e.g. a particular blood vessel, it is reasonable to define the volume of interest in the geometric center between the first and the second volumes. Hence, the volume of interest substantially overlaps with the measurement volume. Assuming a circular like shape of a blood vessel, the geometric center of the first and second volumes and substantially overlaps with the center of the blood vessel that substantially overlap with the center of the measurement volume of the spectroscopic system. Additionally, by making use of a lateral image of a volume of skin, size information of capillary vessels can be obtained and further analyzed for optimizing the autofocus mechanism.

In another aspect, the invention provides a computer program product for a spectroscopic system for determining of a property of a volume of interest. The volume of interest has an optical property that varies with time and the computer program product comprises computer program means for determining the position of the volume of interest on the basis of measuring of an optical property of an at least first and second volume during a first and a second time interval by making use of a measurement unit. The computer program means being further adapted for focusing an excitation beam into the volume of interest by controlling of focusing means and for subsequently detecting return radiation from the volume of interest for spectroscopic analysis.

In still another aspect, the invention provides a method of determining of a position of a volume of interest for determining of a property of the volume of interest by means of a spectroscopic system. The spectroscopic system has focusing means for focusing an excitation beam into the volume of interest and further has detection means for detecting respective return radiation from the volume of interest for spectroscopic analysis. The method of determining the position of the volume of interest comprises the steps of measuring of an optical property of an at least first volume during a first time interval, measuring of an optical property of an at least second volume during a second time interval and determining the position of the volume of interest on the basis of the optical properties of the at least first and second volumes.

In particular, determination of the position of the volume of interest and focusing of the excitation beam can be performed simultaneously. This means that the excitation beam can be focused in an arbitrary volume and that elastically scattered radiation of the excitation beam can be analyzed in order to determine the position of the volume of interest. This position determination can be implemented in a control loop analyzing fluctuations of reflected radiation and subsequently varying the depth of the confocal measurement volume of the excitation beam.

It is to be noted, that the present invention is not restricted to a particular type of spectroscopic techniques, as e.g. Raman spectroscopy, but that other optical spectroscopic techniques can also be used. This includes (i) other methods based on Raman scattering including stimulated Raman spectroscopy and coherent anti-Stokes Raman spectroscopy (CARS), (ii) infra-red spectroscopy, in particular infra-red absorption spectroscopy, Fourier transform infra-red (FTIR) spectroscopy and near infra-red (NIR) diffusive reflection spectroscopy, (iii) other scattering spectroscopy techniques, in particular fluorescence spectroscopy, multi-photon fluorescence spectroscopy and reflectance spectroscopy, and (iv) other spectroscopic techniques such as photo-acoustic spectroscopy, polarimetry and pump-probe spectroscopy. Preferred spectroscopic techniques for application to the present invention are Raman spectroscopy and fluorescence spectroscopy.

Figure 2:
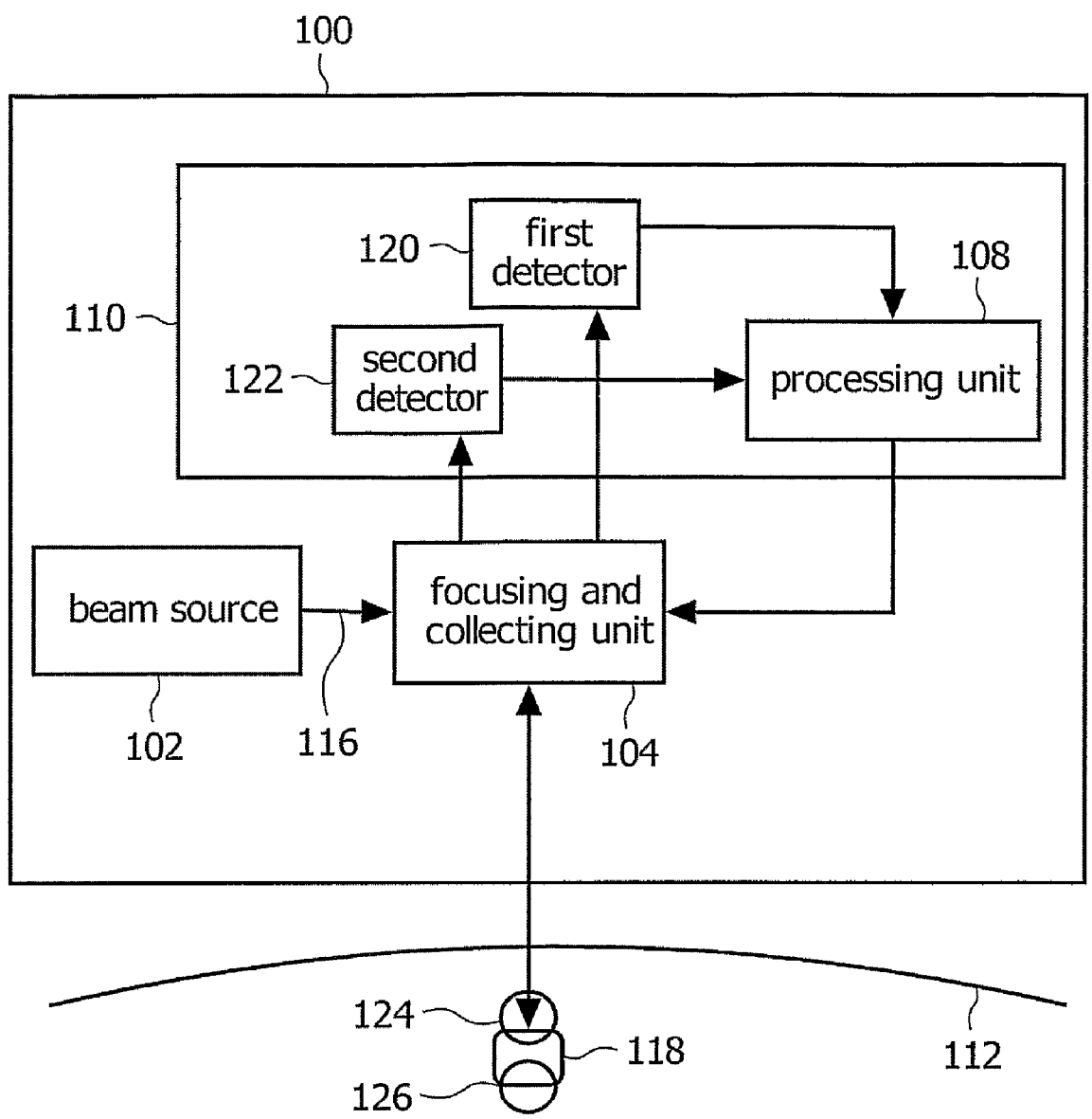
Figure 3:
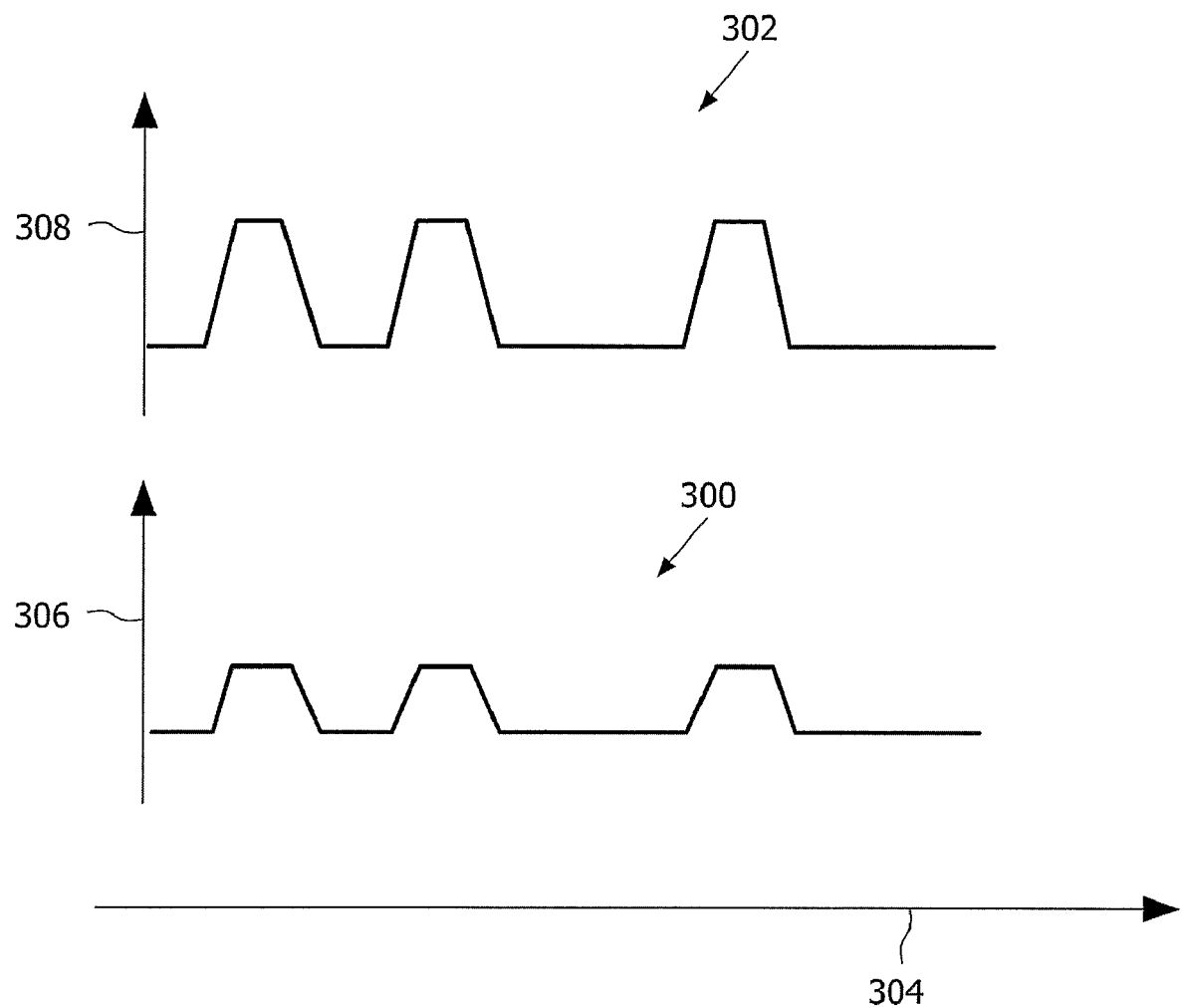
Figure 4:
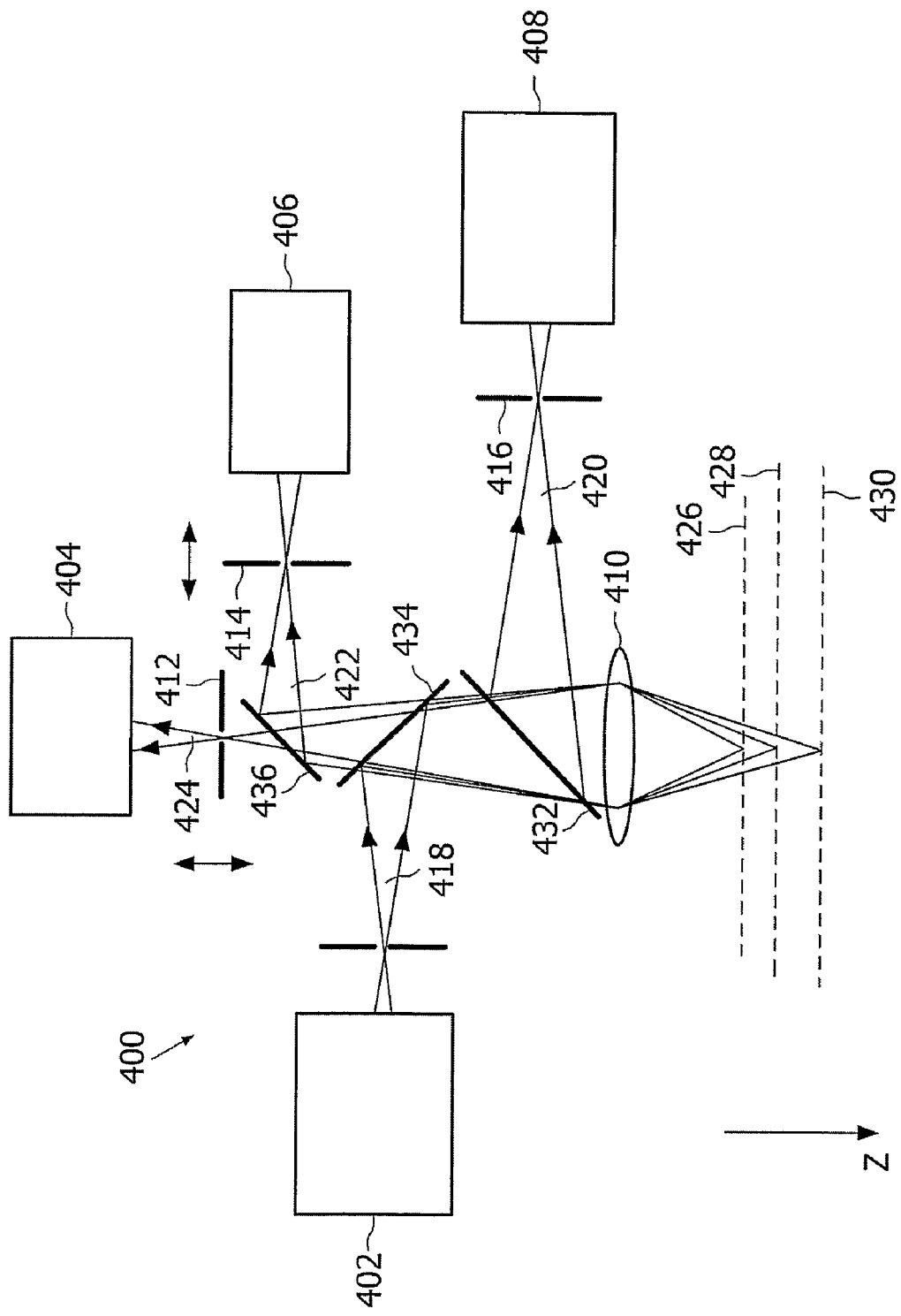
Figure 5:
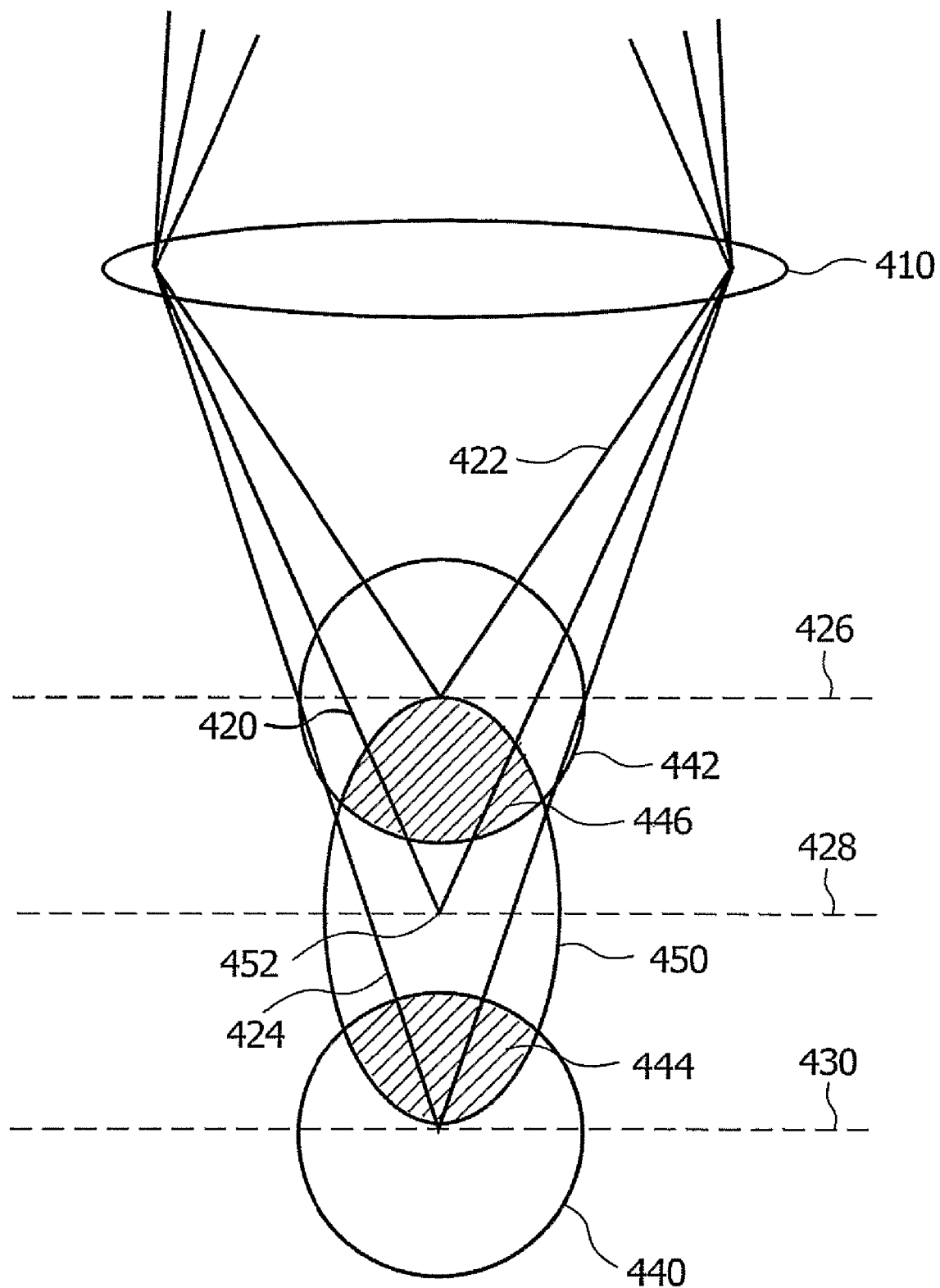

In the following, preferred embodiments of the invention will be described in greater detail by making reference to the drawings in which:

FIG. 1 shows a block diagram of the autofocus system of the spectroscopic system, FIG. 2 is illustrative of a block diagram of an autofocus system making use of a first and a second optical signal emanating from a first and a second volume, FIG. 3 is illustrative of the fluctuations of a first and a second optical signal, FIG. 4 shows a detailed implementation of the autofocus system, FIG. 5 shows a capillary vessel with two partially overlapping volumes.

FIG. 1 shows a block diagram of the autofocus mechanism for a spectroscopic system 100. The autofocus mechanism is adapted to precisely locate a volume of interest 114 underneath the surface of a skin 112. The spectroscopic system 100 has a beam source 102, a measurement unit 110 as well as a focusing and collecting unit 104. Additionally, the spectroscopic system 100 has a spectrometer for spectrally analyzing return radiation from the volume of interest 114. For reasons of simplicity the spectrometer is not illustrated in FIG. 1.

The measurement unit 110 has a detector 106 and a processing unit 108. The beam source 102, typically a laser emitting light in the near infrared range, generates an excitation beam that is directed towards the focusing and collecting unit 104. By means of the focusing and collecting unit 104, the excitation beam 116 is directed towards and focused into the volume of interest 114 underneath the surface of the skin 112.

The inventive autofocus mechanism exploits the fluctuations of the intensity of elastically scattered portions of the excitation beam indicating that the measurement volume at least partially overlaps with a capillary blood vessel. The focusing and collecting unit 104 is also adapted to collect any kind of return radiation emanating from the volume of interest 114.

In particular, portions of the return radiation that are due to elastic scattering, i.e. that do not feature a frequency shift with respect to the excitation radiation are separated from the spectroscopic signals featuring a detectable frequency shift. Elastically scattered radiation, hence radiation being reflected in the volume of interest 114 is provided to the detector 106 of the measurement unit 110. The detector 106 in turn is capable to analyze the fluctuations and in particular the amplitude and/or the intensity of the fluctuations of the reflected radiation. The detector 106 is further connected to the processing unit 108 generating a control signal on the basis of the detected fluctuations.

Depending on the control signal, the processing unit 108 controls the focusing and collecting unit 104 in order to shift the confocal measurement volume of the excitation beam 116. Preferably, the confocal measurement volume is only shifted along the optical axis of the excitation beam 116, i.e. perpendicular to the surface of the skin. In response of shifting the confocal measurement volume, also the magnitude of the fluctuations of the reflected radiation may change. Such a modification is detected by the detector and further analyzed by the processing unit 108. Depending on the modification of the magnitude of the fluctuations of the reflected radiation, the processing unit 108 generates a corresponding control signal.

The focusing and collecting unit 104, the detector 106 and the processing unit 108 form a control loop for maximizing the magnitude, i.e. the amplitude and/or the intensity, of the fluctuations of the reflected radiation emanating from various depths underneath the surface of the skin 112. Various depths of various volumes correspond to various magnitudes in the fluctuations of the reflected radiation. The maximum magnitude of the fluctuations indicate a maximum overlap of a confocal measurement volume and a capillary blood vessel. Vertically scanning through the skin 112 and thereby determining a position of a volume from which maximum intensity of fluctuations of reflected radiation occur allows to precisely determine the depth of the volume of interest 114 with respect to the surface of the skin 112.

FIG. 2 shows a similar embodiment as FIG. 1, wherein the measurement unit 110 has a first detector 120 and a second detector 122. The first detector 120 is arranged in such a way that it only detects radiation being reflected from the first volume 124 and the second detector 122 is arranged in such a way that it only detects radiation emanating from the second volume 126. The first and the second volumes 124, 126 partially overlap with a capillary vessel 118. The volume of interest for the spectroscopic analysis is in the center of the capillary vessel 118.

Blood and in particular red blood cells flowing through the capillary vessel 118 merely feature the same geometric dimension as the first and the second volumes 124, 126. The excitation beam 116 simultaneously irradiates the capillary vessel 118 as well as the first and the second volumes 124, 126. The first detector 120 now in turn only detects light reflected within the first volume 124 and the second detector is adapted to only detect reflected light of the excitation beam emanating from the second volume 126.

The autofocus mechanism now makes explicit use of the fact that red blood cells have a substantially different reflectivity than blood plasma and surrounding tissue. When now a red blood cell passes through the capillary vessel 118, a remarkable increase in reflectivity may be detected. Since the overlap between the first volume 124 and the blood vessel substantially differs from the overlap of the second volume 126 and the blood vessel, the intensity of the reflected light detected by the first detector 120 and the second detector will remarkably vary. In this case, the magnitude of the intensity fluctuation detected by the second detector 122 will be larger than the corresponding magnitude detected by the first detector 120.

Both detectors 120, 122 generate corresponding intensity signals that are passed to the processing unit 108. The processing unit 108 is capable to generate a control or a difference signal on the basis of the two intensity signals obtained from the first and the second detector 120, 122. The processing unit 108 then controls the focusing and collecting unit 104 in order to slightly shift the first volume 124 and the second volume 126 in such a way that the overlap of each volume 124, 126 with the capillary vessel 118 becomes substantially equal. Assuming a circular like shape of the capillary vessel 118, the geometric center between the first volume 124 and the second volume 126 specifies the center of the capillary vessel 118. In this way, the two volumes 124, 126 effectively specify the position of the volume of interest.

FIG. 3 is illustrative of two intensity signals 300, 302 that are produced by the first and the second detector 120, 122 of FIG. 2. Moreover, FIG. 3 illustrates the intensity fluctuations of the two intensity signals 300, 302. The horizontal axis of the diagram of FIG. 3 304 specifies the time and the two vertical axis 306, 308 specify the amplitude of each signal 300, 302. As can be seen in the diagram, the first signal 300 as well as the second signal 302 are subject to irregular fluctuations. The fluctuations of the two signals 300, 302 occur simultaneously but are different in magnitude. Here, the fluctuations of the second signal 302 are larger than the fluctuations of the first signal 300 indicating that the degree of overlap between the second volume 126 and the capillary vessel 118 is larger than the degree of overlap between the first volume 124 and the capillary vessel 118.

The autofocus mechanism aims to minimize the difference in magnitude of the two signals 300, 302 resulting in an equal overlap between the first and second volumes 124, 126 and the capillary vessel 118 allowing for precise determination of the center of the capillary vessel 118.

By monitoring the first signal 300 and the second signal, and in particular the frequency of the arising intensity fluctuations it can be effectively guaranteed that the two signals refer to volumes that overlap with a common capillary vessel. Otherwise, the frequency of the fluctuations would be rather uncorrelated.

FIG. 4 illustrates a detailed embodiment of the autofocus system for the spectroscopic system 400. The spectroscopic system 400 has a laser 402, a first detector 404, a second detector 406, a spectrometer 408, a focusing unit 410, three pinholes 412, 414, 416, a dichroic mirror 432 and two beam splitters 434, 436.

The laser 402 generates an excitation beam 418 that is reflected by the beam splitter 434 and directed towards the focusing unit 410. Preferably, the reflected part of the excitation beam 418 is focused into the focal plane of interest 428 by the focusing unit 410. However, regions lying within the first focal plane 430 and within the second focal plane 426 are also irradiated by the excitation beam.

The measurement system for determining the volume of interest consists of the first detector 404, the second detector 406 as well as the pinhole 412 and the pinhole 414. The components of the measurement unit and in particular the pinhole 412 and the first detector 404 are arranged in such a way that the detector 404 only detects radiation that is elastically scattered from a volume around the first focal plane 430. Similarly, the second detector 406 and the pinhole 414 are arranged in such a way that the second detector 406 only detects elastically scattered radiation of the excitation beam that is elastically scattered from a volume around the second focal plane 426.

The system of beam splitters 436, 434 and the dichroic mirror 432 are designed in such a way that inelastically scattered radiation 420 is reflected at the dichroic mirror 432 and directed through the pinhole 416 to the spectrometer 408. Elastically scattered radiation of the excitation beam 418 is basically transmitted through the dichroic mirror 432 and distributed via the beam splitter 436 to the two detectors 404, 406.

Here, the first measurement return radiation 424 detected by the first detector 404 is indicative of a partial spatial overlap of the volume around the first focal plane 430 and a capillary vessel and the second measurement return radiation 422 that is detected by the second detector 406 is indicative of an overlap between a volume surrounding the second focal plane 426 and a capillary vessel. The detectors 404, 406 that are preferably implemented as photo diodes are adapted to generate a signal that is indicative of the magnitude of intensity fluctuations of the first and the second measurement return radiation 424, 422.

The pinholes 412, 414 are adapted to be moveable along the optical axis of the first and the second measurement return radiation 424, 422. In this way, the center of the confocal measurement volume specified by the first and by the second focal planes 430, 426 can be arbitrarily shifted. Pinhole 412 and/or pinhole 414 or both pinholes can be shifted simultaneously in order to adapt the magnitude of the fluctuations of the first and the second measurement return radiation. This adaptation inherently specifies the center of the capillary vessel. Since the position of each pinhole 412, 414, 416 specifies a vertical position of each of the focal planes 426, 428 and 430, the position of the center of the capillary vessel can precisely be determined.

Having once knowledge of the location of the volume of interest either allows to shift the pinhole 416 for moving the confocal measurement volume of the spectrometer 408 into the center of the capillary vessel or alternatively allows to move the focusing unit 410 in such a way that the focal plane of interest 428 overlaps with the center of the capillary vessel.

In order to allow a greater flexibility for shifting the various focal planes 426, 428, 430 not only the pinholes and the focal plane but also the two detectors 404, 406 are adapted to be moveable along the optical axis of their respective measurement return radiation.

In particular making use of the described autofocus mechanism in combination with a lateral imaging of a volume underneath the surface of the skin allows to adapt the autofocus mechanism to various blood vessels of different size. For example by acquiring a two dimensional lateral image of a volume of the skin featuring a large depth of focus allows for detection of a blood vessel and for lateral positioning of the skin with respect to the spectroscopic system. The lateral image of the blood vessel can now further be exploited to determine the size of the blood vessel allowing for adjusting the separation of the first and the second focal planes 430, 426 that represent an optimum separation for the particular size of the detected blood vessel.

FIG. 5 shows an enlarged view of the focal planes 426, 428 and 430 and the focusing unit 410. The elliptic region 450 represents a capillary vessel. The center of the volume of interest 452 is located around the center of the capillary vessel 450 and specifies the location from where the return radiation 420 to be detected by the spectrometer 408 has to ideally emanate. The first focal plane 430 specifies a first volume 440 and the second focal plane 426 specifies a second volume 442. The pinholes 412 and 414 are arranged in such a way, that the first detector 404 only collects first measurement return radiation 424 emanating from the first volume 440.

Similarly, the pinhole 414 is arranged in such a way, that the detector 406 only collects second measurement return radiation 422 around the second volume 442. The shaded volumes denoted as first overlap 444 and second overlap 446 illustrate the partial overlapping between the first and the second volumes 440, 442 with the capillary vessel 450. Assuming that blood cells are flowing through the capillary vessel a corresponding fluctuation being proportional to the overlap 444, 446 will be detectable by the separate detectors 404, 406.

Further it is to be noted, that the present invention may not only be applied in combination with a vertical arrangement of various planes of focus (426, 428, 430). Determination of position of a volume of interest may also refer to optical inspection of volumes that are arbitrarily located in a way that they partially overlap with the volume of interest. Therefore, the present invention may also be realized in a horizontal or somehow skewed configuration. The at least first and second volumes therefore do not have to be located on a straight line, as for example the optical axis of the spectroscopic system.

LIST OF REFERENCE NUMERALS 100 spectroscopic system
102 beam source
104 focusing and collecting unit
106 detection unit
108 processing unit
110 measurement unit
112 skin
114 volume of interest
116 excitation beam
118 capillary vessel
120 first detector
122 second detector
124 first volume
126 second volume
300 first signal
302 second signal
304 time axis
306 amplitude
308 amplitude
400 spectroscopic system
402 laser
404 first detector
406 second detector
408 spectrometer
410 focusing unit
412 pinhole
414 pinhole
416 pinhole
418 excitation beam
420 return radiation
422 second measurement return radiation
424 first measurement return radiation
426 second focal plane
428 focal plane of interest
430 first focal plane
432 dichroic mirror
434 beam splitter
436 beam splitter
440 first volume
442 second volume
444 first overlap
446 second overlap
450 capillary vessel
452 volume of interest

The invention claimed is:

1. A spectroscopic system for determining a property of a volume of interest, the volume of interest having an optical property varying with time, the spectroscopic system comprising:
an excitation unit configured to generate an excitation beam;
a focusing unit configured to focus the excitation beam into the volume of interest;
a measurement unit configured to determine a center of the volume of interest based on temporally varying optical measurements from at least a first portion and a second portion of the volume of interest during a first time interval and second time interval; and a spectrometer focused to detect return radiation from the center of the volume of interest for spectroscopic analysis.

2. The spectroscopic system according to claim 1, wherein the measurement unit detects at least a first and a second temporally varying measurement return radiation from the at least first and second portions, the at least first and second measurement return radiation being indicative of a time varying optical property of the at least first and second portions.

3. The spectroscopic system according to claim 1, wherein the first and second time intervals either completely coincide or partially coincide or wherein the first and second time intervals define two non-coinciding sequential time intervals.

4. The spectroscopic system according to claim 2, wherein the measurement unit determines a maximum value of temporal variations of the at least first and second measurement return radiation.

5. The spectroscopic system according to claim 4, wherein the measurement unit determines a difference between the values of temporal variations of the at least first and the second measurement return radiation.

6. The spectroscopic system according to claim 2, wherein the measurement radiation and the excitation beam are generated by the same optical source, and wherein the focusing unit further directs the measurement radiation beam into the at least first and second portions.

7. The spectroscopic system according to claim 2, wherein the measurement unit detects both first and second measurement return radiation and comprises at least one detector element and at least one aperture element forming an aperture for each of the first and second measurement return radiation.

8. The spectroscopic system according to claim 7, wherein the at least one detector element and the at least one aperture element are moveable along the optical axis of the return radiation.

9. The spectroscopic system according to claim 7, wherein the position of the first and second portions are determined on the basis of a position of the respective aperture element.

10. The spectroscopic system according to claim 3, wherein the first and the second portions are located on the optical axis of the excitation beam.

11. The spectroscopic system according to claim 3, wherein the first and the second portions are substantially equidistantly separated from the center of the volume of the spectroscopic system.

12. A computer program product for a spectroscopic system for determining of a property of a volume of interest, the volume of interest having an optical property varying with time, the computer program product storing a computer program which controls a processor to perform the steps of:

determining a center of the volume of interest based on measurements of a time varying optical property of at least first return radiation from a first portion and second return radiation from a second portion of the volume of interest during a first and second time interval, the time varying optical property varying over the first and second intervals, focusing an excitation beam into the volume of interest by controlling of focusing unit, detecting return radiation from the center of the volume of interest, and spectroscopically analyzing the return radiation from the center of the volume of interest.

13. A method of determining a location of a volume of interest which is to be analyzed by a spectroscopic system to determine a property of the volume of interest, the spectroscopic system having a focusing unit which focuses an excitation beam into the volume of interest and a detection unit which detects return radiation from the volume of interest for spectroscopic analysis, the method of determining the location of the volume of interest comprising the steps of:

measuring a time varying optical property of at least a first subregion of the volume of interest during a first time interval, the optical property varying during the measuring, measuring of a time varying optical property of at least a second subregion of the volume of interest during a second time interval, the optical property varying during the measuring, determining the location of the volume of interest on the basis of the time varying optical properties of the at least first and second subregions of the volume of interest.

14. The method according to claim 13, wherein the first and second time intervals at least one of:

completely coincide or partially coincide, and define two non-coinciding sequential time intervals.

15. A method for determining a location of a volume of interest which has an optical property varying with time comprising:

measuring a temporally varying optical property of a first portion of the volume of interest during a first time interval, the optical property varying over the first time interval;

measuring a temporally varying optical property of a second portion of the volume of interest during a second time interval, the optical property varying over the second time interval;

determining a difference between the temporally varying optical property measured for the first portion of the volume of interest and the temporally varying optical property measured for the second portion of the volume of interest; and determining the location of the volume of interest based on the difference determined.

16. The method of claim 15, further including:

varying a position of at least one of the first portion and the second portion of the volume of interest in order to minimize the difference determined.

17. The method of claim 15, further including:

varying the position of at least one of the first portion of the volume of interest and the second portion of the volume of interest to substantially equalize the measured optical property of the first portion of the volume of interest and the measured optical property of the second portion of the volume of interest.

18. The method of claim 15 further comprising determining a property of the volume of interest via a spectroscopic system.

19. A system for determining a position of a volume of interest having an optical property varying with time comprising:

means for measuring the optical property of a first portion of the volume of interest during a first time interval, the optical property varying over the first time interval;

means for measuring an optical property of a second portion of the volume of interest during a second time interval, the optical property varying over the second time interval;

means for determining a difference between the optical property measured for the first portion of the volume of interest and the optical property measured for the second portion of the volume of interest; and means for determining the position of the volume of interest based on the difference determined.

20. The system of claim 19 further comprising:
means for changing a position of at least one of the first portion of the volume of interest and the second portion of the volume of interest to make the measured optical property of the first portion of the volume of interest substantially equal to the measured optical property of the second portion of the volume of interest.

* * * * *